United States Patent
Fujii et al.

(10) Patent No.: US 8,946,303 B2
(45) Date of Patent: *Feb. 3, 2015

(54) FATIGUE REDUCING AGENT

(75) Inventors: Kenji Fujii, Kobe (JP); Taizo Kawabe, Himeji (JP); Kazunori Hosoe, Takasago (JP); Takayoshi Hidaka, Kobe (JP)

(73) Assignee: Kaneka Corporation, Osaka (JP)

( * ) Notice: Subject to any disclaimer, the term of this patent is extended or adjusted under 35 U.S.C. 154(b) by 1723 days.

This patent is subject to a terminal disclaimer.

(21) Appl. No.: 10/541,020

(22) PCT Filed: Jan. 19, 2004

(86) PCT No.: PCT/JP2004/000366
§ 371 (c)(1),
(2), (4) Date: Jun. 28, 2005

(87) PCT Pub. No.: WO2004/066988
PCT Pub. Date: Aug. 12, 2004

(65) Prior Publication Data
US 2006/0165672 A1    Jul. 27, 2006

(30) Foreign Application Priority Data
Jan. 31, 2003  (JP) ................ 2003-024758

(51) Int. Cl.
*A61K 31/122*  (2006.01)
*A61K 38/43*  (2006.01)
*A61K 38/44*  (2006.01)
*A61K 31/09*  (2006.01)

(52) U.S. Cl.
CPC ............. *A61K 31/09* (2013.01); *A61K 31/122* (2013.01)
USPC ............... 514/689; 424/94.1; 424/94.4

(58) Field of Classification Search
CPC ..... A61K 31/05; A61K 31/122; A61K 38/43; A61K 38/44
USPC ................ 514/689; 424/94.1, 94.4
See application file for complete search history.

(56) References Cited

U.S. PATENT DOCUMENTS

| | | | |
|---|---|---|---|
| 4,068,003 A | 1/1978 | Miyata | |
| 6,184,255 B1 | 2/2001 | Mae et al. | |
| 6,444,221 B1 | 9/2002 | Shapiro | |
| 7,015,252 B2 * | 3/2006 | Fujii et al. | 514/690 |
| 2004/0115181 A1 * | 6/2004 | Fujii et al. | 424/94.1 |

FOREIGN PATENT DOCUMENTS

| | | |
|---|---|---|
| CA | 2406570 A1 | 10/2002 |
| DE | 19806947 A1 | 8/1999 |
| JP | 52-99222 A | 8/1977 |
| JP | 7-330584 A | 12/1995 |
| JP | 7-330593 A | 12/1995 |
| JP | 10-53520 A | 2/1998 |
| JP | 10-287560 A | 10/1998 |
| JP | 2002-363073 A | 12/2002 |
| JP | 2003-119127 A | 4/2003 |
| WO | WO 98/07417 A | 2/1998 |
| WO | 9843617 A1 | 10/1998 |
| WO | 0057871 A | 10/2000 |
| WO | 0101962 A1 | 1/2001 |
| WO | 0132040 A | 5/2001 |
| WO | 0137788 A1 | 5/2001 |
| WO | 0152822 A1 | 7/2001 |
| WO | WO 01/85156 | 11/2001 |
| WO | WO 02/092067 | * 10/2002 |
| ZA | 200109677 A | * 9/2002 |

OTHER PUBLICATIONS

"Fatigue". Merriam-Webster's Collegiate Dictionary (Tenth Edition). Merriam-Webster Inc., 1996. p. 424.*
Staub et al. "Fatigue after Stroke: A Major but Neglected Issue". Cerebrovascular Disease, 2001; 12(2):75-81.*
Wilson et al. "Exertional Fatigue Due to Skeletal Muscle Dysfunction in Patients with Heart Failure". Circulation, 1993; 87:470-475.*
Osol A. [Editor] Remington's Pharmaceutical Sciences (Fifteenth Edition), Mack Publishing. 1975. p. 712.*
Jacob L. "General Pharmacologic Principles". Pharmacology (Fourth Edition). Williams and Wilkins Company, 1996. p. 1-13.*
Werbach, Nutritional Strategies for Treating Chronic Fatigue Syndrome, *Alternative Medicine Review* 5:93-108 (2000).
Машковский М.Д., , Лекарственные средства, , М., ООО «Новая волна», , 2001, т. 2, стр. 187.
Mashkovsky, M.D., "Drug—Medicinal Compound," M, OOO, *New Wave* 2:187 (2001).
O. Hanninen, M. Atalay, D. Laaksonen, C.K Sen; "Muscle activity and radicals"; Pfluegers Archiv European Journal of Physiology, vol. 443, NO. Supplement 2, Mar. 2002, p. S371, XP002478085.
J. Racek et al; "Ubiquinol Q-10 (coenzyme Q-10)"; Database Embase [Online]; Elsevier Science Publishers, Amsterdam, NL; 1999, XP002478080, abstracting *Klinicka Biochemie a Metabolismus*, 7(2):92-95 (1999).

* cited by examiner

*Primary Examiner* — Golam M M Shameem
*Assistant Examiner* — Laura Daniel
(74) *Attorney, Agent, or Firm* — Sughrue Mion, PLLC

(57) ABSTRACT

To maintain physical fitness and health of middle-aged and older persons living in the threshold of the aging society, the present invention provides a fatigue reducing agent which is highly effective for preventing and reducing fatigue, wherein the agent is made of a composition of substances that are very safe so that long-term administration is possible. A composition containing reduced coenzyme Q was found to be effective for preventing and reducing fatigue, including muscle fatigue. Since the fatigue reducing effect of the composition of the present invention is seen not only in young rats but also more pronounced in aged rats, the present invention can provide the fatigue reducing agent which is very useful, especially, for middle-aged and older persons as well as for young people.

4 Claims, No Drawings

FATIGUE REDUCING AGENT

TECHNICAL FIELD

The present invention relates to a fatigue reducing agent comprising a reduced coenzyme Q represented by the following formula (1), or a reduced coenzyme Q represented by the following formula (1) and an oxidized coenzyme Q represented by the following formula (2) as active ingredients (wherein n represents an integer from 1 to 12)

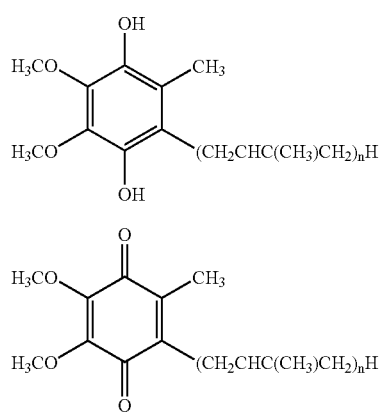

Here, a fatigue reducing agent is a composition which helps in the recovery from and also in the prevention of physical exhaustion caused by exercise, relieves physical exhaustion during and after sickness, and reduces fatigue caused by aging.

BACKGROUND ART

Worsening of physical fitness caused by aging manifests itself in the symptoms of fatigue. A vicious cycle takes place in which fatigue causes lack of physical activity, which, in turn, induces the loss of muscle strength. The loss of muscle strength may cause bone fractures due to falling or may result in a bedridden condition. Therefore, in order to enjoy a fruitful and comfortable old age, it is important to relieve fatigue and to prevent the loss of muscle strength as much as possible.

In the past, many agents for recovery from fatigue have been marketed. However, most of these agents have been prescribed as stimulants for young persons or young athletes, and there were none that middle-aged and older persons could use safely for continuously over a long period of term to maintain health and physical fitness.

Coenzyme Q is an essential component and distributed widely in living organisms from bacteria to mammals. In humans, it is known that coenzyme $Q_{10}$, which is coenzyme Q with 10 repeated units in the side chain, is the main component. Coenzyme $Q_{10}$ is a physiological component present as a constitutive component of the electron transport system of the mitochondria in cells of living organisms and functions as a transport component of the electron transport system by repeating oxidation and reduction in the living organism. Coenzyme Q is known to show activities in energy production, membranestabilization, andantioxidation, anduseful-widely. The oxidized coenzyme $Q_{10}$ (ubiquinon or ubide-carenon) has been known to act effectively on the heart, and it has been used in pharmaceutical application as an agent for congestive heart failure. Its effects on improving the oxygen availability in the heart muscle, activation of ATP production in the heart muscle, improvement on heart functions and the like, have been reported. Other than for the pharmaceutical application, its effects as a nutrient and a nutritional supplement, like vitamins, have been reported. Further, Japanese Patent Laid-Open No. 62-59208 reports a composition for activating tissue metabolism comprising a mixture of the oxidized coenzyme $Q_{10}$ (ubiquinon) and dried yeast powder, Japanese Patent Laid-Open No. 52-99220 reports improvements in symptoms of myasthenia gravis using the oxidized coenzyme $Q_{10}$, and Japanese Patent Laid-Open No. 52-99222 reports increased red blood cell counts using the oxidized coenzyme $Q_{10}$. Still further, its effect of recovery from fatigue using the oxidized coenzyme $Q_{10}$ has been reported (Japanese Patent Laid-Open No. 7-330584, Japanese Patent Laid-Open No. 7-330593 and Japanese Patent Laid-Open No. 10-287560).

Unlike oxidized coenzyme $Q_{10}$, however, there has been no report as to the usefulness of reduced coenzyme $Q_{10}$. This is due to the fact that since reduced coenzyme $Q_{10}$ is readily oxidized by air, its usefulness could not be evaluated. Another reason why the usefulness of reduced coenzyme $Q_{10}$ has not been evaluated is that the effects of oxidized coenzyme $Q_{10}$ and reduced coenzyme $Q_{10}$ on the living organisms are considered to be equivalent because, it is known that reduced coenzyme $Q_{10}$ increases in general, due to reduction in living organisms even following administration of oxidized coenzyme $Q_{10}$. We have disclosed earlier in Japanese Patent Laid-Open No. 10-109933 that the oral absorption of coenzyme $Q_{10}$ is increased when both oxidized coenzyme $Q_{10}$ and reduced coenzyme $Q_{10}$ coexist as compared to when oxidized coenzyme $Q_{10}$ alone exists. We showed that the use of reduced coenzyme $Q_{10}$ is very effective in increasing the oral absorption for various applications. However, there has been no information on whether or not there is any difference in anti-fatigue effect between oxidized coenzyme $Q_{10}$ and reduced coenzyme $Q_{10}$.

The objective of the present invention is to develop a composition which is effective for reducing and preventing physical fatigue and which is safe for continuous and long-term administration in middle-aged and older persons.

DISCLOSURE OF THE INVENTION

To solve the above mentioned problem, the present inventors have intensively performed research on fatigue reducing or preventing agents that contain reduced coenzyme Q, discovered that agents containing reduced coenzyme Q were more effective for reducing fatigue than those containing oxidized coenzyme $Q_{10}$ alone, and completed the present invention. Thus the present invention relates to a fatigue reducing agent characterized in that it contains reduced coenzyme Q, or reduced coenzyme Q and oxidized coenzyme Q, as active ingredients. Further, it has been found that the effect of reducing fatigue obtained by containing reduced coenzyme $Q_{10}$ is more remarkable with advancing age. This result is appeared to indicate that this agent is effective for middle-aged and older persons who are easily fatigued and have difficulty in maintaining good health.

DETAILED DISCLOSURE OF THE INVENTION

It is known that usually around 40 to 90% of coenzyme Q exists in the reduced form in living organisms. The process for obtaining reduced coenzyme Q is not limited in particular. For example, after obtaining coenzyme Q by the conventionally known methods, such as chemical synthesis, fermentation, extraction from natural products and the like, the reduced coenzyme Q fraction in the effluent is concentrated by chromatography. In this case, if necessary, concentration by chromatography may be conducted after reducing oxidized coenzyme Q in the above mentioned coenzyme Q preparation by a conventional method, such as by adding an ordinary reducing agent, such as sodium borohydride, sodium dithionite (sodium hydrosulfite) and the like. Further, reduced coenzyme Q may be obtained by reacting existing highly purified coenzyme Q with the above mentioned reducing agents. Alternatively, microbial cells and the like containing reduced coenzyme Q may be used.

Normally, the proportion of reduced coenzyme Q in a coenzyme Q preparation may be estimated by measuring the quantities of oxidized coenzyme Q and reduced coenzyme Q in a sample by using a HPLC system equipped with a UV detector and calculating the ratio of the quantities, or it can be obtained by calculating the ratio of the peak areas of oxidized coenzyme Q and reduced coenzyme Q by a HPLC system with an incorporated electrochemical detector. The system with the electrochemical detector is very useful for measuring the ratio of reduced coenzyme Q, which is present in a very small amount in living organisms or in test samples, because the system can measure oxidized coenzyme Q and reduced coenzyme Q with specificity andhighsensitivity. All data-ontheproportion of reduced coenzyme Q shown in the present invention have been obtained by the HPLC system with the electrochemical detector.

Since coenzyme Q is involved in energy production, increasing the level of coenzyme Q in the body is thought to be effective in reducing fatigue. In particular, reduced coenzymeQ, unlikeoxidizedcoenzymeQ, exhibitsantioxidation activity and is expected to protect tissues from oxidative stress and oxidative stress related damages. Consequently, increasing the level of reduced coenzyme Q is considered to be very effective in improving recovery from fatigue, especially in regions where a large amount of energy is required by the muscle and where the influence of oxidative stress caused by energy production tends to accumulate.

As described above, we found that oral administration of reduced coenzyme Q raised the plasma level of coenzyme Q more than oral administration of oxidized coenzyme $Q_{10}$, but it was not clear whether the level of reduced coenzyme $Q_{10}$ was increased in the body. Conventionally, it has been believed that the effect on the living body is substantially the same between oxidized coenzyme Q and reduced coenzyme Q with no difference, because oxidized coenzyme Q administered is reduced to reduced coenzyme Q in vivo. However, this time, we measured the intramuscular level of reduced coenzyme Q and obtained the results that the intramuscular level of reduced coenzyme Q increased after administration of reduced coenzyme Q but decreased after administration of oxidized coenzyme Q. These results indicate that the protective effect of reduced coenzyme Q against oxidative stress in the muscle is vastly different from that of oxidized coenzyme Q, suggesting that administration of reduced coenzyme Q is more preferable for protecting muscle damage caused by exercise and for reducing fatigue. To our surprise, we found that endogenous coenzyme Q can be increased by administration of reduced coenzyme Q. Here, endogenous coenzyme Q is not the one administered from outside but the one synthesized in vivo. We confirmed the increase of endogenous coenzyme Q by administering reduced coenzyme $Q_{10}$, and this is probably due to activation of the biosynthesis of coenzyme Q or protection of the metabolism.

Therefore, the fatigue reducing agent of the present invention is able to increase the level of coenzyme Q in the muscles of animals, vertebrates, mammals and humans. The fatigue reducing agent of the present invention can increase the level of reduced coenzyme Q in the muscles of animals, vertebrates, mammals and humans.

Methods for increasing the level of 2 kinds of above mentioned coenzyme Q provides methods for reducing fatigue of animals, vertebrates, mammals and humans.

The fatigue reducing agent of the present invention is effective for reducing and preventing physical fatigue and can be taken by not only young people but also middle-aged and older persons. Further, the fatigue reducing agent of the present invention is more valuable especially for middle-aged and older persons.

The content of reduced coenzyme Q in the fatigue reducing agent of the present invention is not limited in particular, but can be set appropriately according to the concept of the product. By increasing the ratio of reduced coenzyme Q to an extremely high level, higher efficacy of the agent may be expected, although the cost may also increase due to the need for the measures for stabilization.

The proportion of reduced coenzyme Q to the total coenzyme Q in the fatigue reducing agent of the present invention can be determined appropriately according to the concept of the product. By increasing the ratio of reduced coenzyme Q to an extremely high level, higher efficacy of the agent may be expected, although the cost may also increase due to the need for the measures for stabilization.

In the fatigue reducing agent of the present invention, a mixture of reduced coenzyme Q and oxidized coenzyme Q may be used an active ingredient. The ratio of reduced coenzyme Q and oxidized coenzyme Q is not limited in particular, but preferably the ratio of reduced coenzyme Q to total coenzyme Q is equal to or above 60% by weight and equal to or below 100% by weight, and more preferably equal to or above 80% by weight and equal to or below 99.5% by weight.

Reduced coenzyme Q, which has 1 to 12 repeated units (n in the formula) in the side chain as shown in the formula (1) described above, may be used in the present invention, but the one with 10 repeated units, that is coenzyme $Q_{10}$, may be used preferably.

The dosage form of the fatigue reducing agent of the present invention is not limited in particular, but may be an oral formulation or an ointment that is applied directly to the skin. The oral formulation may be, for example, a powder formulation, a granule formulation containing a binder, or a capsule formulation obtained by filling capsules with the powder or the granule formulation. Further, natural oils, oily higher fatty acids, higher fatty acid monoglycerides, surfactants, or mixtures thereof may be added and a soft capsule formulation may be prepared by filling capsules with these oily substances. In this case, gelatin, other water soluble high molecules or the like may be used as a main substance. These capsules also include a microcapsule. Alternatively a drinkable formulation may be prepared by liquefying.

In addition to reduced coenzyme Q described above, other pharmaceutically acceptable formulation substances may be optionally added to and mixed into the fatigue reducing agent of the present invention by a conventional method. These substances are not limited in particular, but include, for example, an excipient, a disintegrator, a lubricant, a binder, an antioxidant, a coloring agent, an anticoagulant, an absorbefacient, a solubilizer, a stabilizer and the like.

The excipient described above is not limited in particular, but includes, for example, white sugar, lactose, glucose, corn starch, mannitol, crystalline cellulose, calcium phosphate, calcium sulfate and the like. The disintegrator described above is not limited in particular, but includes, for example, starch, agar, calcium citrate, calcium carbonate, sodium hydrogen carbonate, dextrin, crystalline cellulose, carboxymethylcellulose, tragant and the like.

The lubricant described above is not limited in particular, but includes, for example, talc, magnesium stearate, polyethylene glycol, silica, hydrogenated vegetable oil and the like. The binder described above is not limited in particular, but includes, for example, ethylcellulose, methylcellulose, hydroxypropylmethylcellulose, tragant, shellac, gelatin, gumarabic, polyvinylpyrrolidon, polyvinyl alcohol, polyacrylic acid, polymethacrylic acid, sorbitol and the like.

The antioxidant described above is not limited in particular, but includes, for example, ascorbic acid, tocopherol, vitamin A, β-carotene, sodium dithionite, sodium thiosulfate, sodium pyrosulfate, citric acid and the like.

The coloring agent described above is not limited in particular, but includes, for example, substances that are permitted to add to pharmaceuticals may be used.

The anticoagulant described above is not limited in particular, but includes, for example, stearic acid, talc, light silicic acid anhydride, hydrated silicate dioxide and the like.

The absorbefacient described above is not limited in particular, but includes, for example, surfactants such as higher alcohols, higher fatty acids, glycerin fatty acid esters and the like.

The solubilizer described above is not limited in particular, but includes, for example, organic acids such as fumaric acid, succinic acid, malic acid and the like. The stabilizer described above is not limited in particular, but includes, for example, benzoic acid, sodium benzoate, ethyl paraoxybenzoate and the like.

The formulation is not limited in particular when the agent is applied directly to the skin but, for example, the following formulations may be used: a cream, a paste, a jelly, a gel, an emulsion or a liquid formulation (an ointment, a liniment, a lotion, a cream, a spray and the like) in which the agent substances described above are dissolved, or mixed and dispersed in a suitable base; a formulation in which the agent substances are dissolved, or mixed and dispersed in a base, and spread over a support medium (a poultice and the like); a formulation in which the agent substances described above are dissolved, or mixed and dispersed in a sticker and spread over a support medium (a plaster, a tape and the like). The bases and the stickers, which are normally used in pharmaceuticals and cosmetics, may be used at need as long as the efficacy of the present invention is not impaired.

The fatigue reducing agent of the present invention may also contain an antioxidant or an antioxidant enzyme. The antioxidant is not limited in particular, but, for example, vitamin E, vitamin E derivatives, vitamin C, vitamin C derivatives, probucol, lycopene, vitamin A, carotenoids, vitamin B, vitamin B derivatives, flavonoids, polyphenols, glutathione, pyrroloquinoline quinone, pycnogenol, flavangenol, or selenium may be suitable. The antioxidants described above may be used singly or as a mixture of the two or more. The antioxidant enzyme is not limited in particular, but, for example, superoxide dismutase (SOD), glutathione peroxidase, glutathione-S-transferase, glutathione reductase, catalase or ascorbic acid peroxidase may be suitable. The antioxidant enzymes described above may be used singly or as a mixture of the two or more.

The fatigue reducing agent of the present invention may also contain other nutrient and tonic components. The nutrient and tonic components are not limited in particular, but, for example, creatine, taurine, vitamin $B_1$, vitamin B derivatives, or amino acids may be suitable. The nutrients and tonics described above may be used singly or as a mixture of the two or more. An additive or a synergetic effect may be expected by mixing the coenzyme Q of the present invention with these components.

The fatigue reducing agent of the present invention may also contain nutritional supplements. The nutritional supplements are not limited in particular, but include amino acids, metal ions, sugars, proteins, fatty acids, vitamins and the like. When an ordinary food is made from the fatigue reducing agent of the present invention, the form of the food is not limited in particular, but includes: oil and fat compositions for food, cooking oils, spray oils, butters, margarines, shortenings, whipped creams, condensed milks, whiteners, dressings, pickles, breads, cakes, pies, cookies, Japanese sweets, snack foods, fried snack foods, chocolates and chocolate candies, rice cookies, roux, sauces, Japanese barbecue sauces, toppings, ice candies, noodles, bakery mixes, fried foods, processed meat products, fish cakes, frozen foods such as frozen entrees, frozen meat products, frozen farm products, cooked rice products, jams, cheeses, cheese foods, cheese-like foods, chewing gums, candies, fermented milk products, canned foods, drinks and the like.

The fatigue reducing agent of the present invention may reduce muscle fatigue by being applied directly to the skin. In this case, an anti-inflammatory substance may be included in the formulation. The anti-inflammatory substance is not limited in particular, but at least one may be selected from the group consisting of: steroids, salicylic acid and its derivatives, aryl acetate and its derivatives, propionic acid and its derivatives, fenamic acid and its derivatives, pyrazolone and its derivatives, oxicam and its derivatives, and non-acidic anti-inflammatory agents. Steroids include, for example, prednisolone valerate acetate, amcinonide, diflucortolone valerate, dexamethasone valerate, crobetasol propionate, diflorasone diacetate, dexamethasone propionate, bethamethasone dipropionate, difluprednate, fluocinonide, halcinonide, budesonide, hydrocortisone lactate propionate, betamethasone valerate, beclomethasone dipropionate, fluocinoloneacetonide, triamcinoloneacetonide, flumetasone pivalate, hydrocortisone lactate, clobetasone butyrate, alclomethasone dipropionate, dexamethasone, methylpredonisolone acetate, predonisolone, hydrocortisone acetate. Salicylic acid derivatives include, for example, aspirin and its derivatives, and diflunisal. Aryl acetate derivatives include, for example, indomethacin, diclofenac, sulindac, nabumetone, proglumetacin, indometacin farnesyl, and etodolac. Propionate derivatives include, for example, ibuprofen, naproxen, flurbiprofen, fenoprofen, tiaprofen, pranoprofen, loxoprofen and alminoprofen. Fenamic acid derivatives include, for example, mefenamic acid, tolfenamic acid, and the like. Pyrazolone derivatives include, for example, phenylbutasone, oxyfenbutasone and the like. Oxicam derivatives include, for example, piroxicam, tenoxicam, ampiroxicam and the like. Non-acidic anti-inflammatory agents include, for example, epirizole, tiaramide, emorfazone, and the like. An additive or a synergetic effect may be expected by mixing the fatigue reducing agent of the present invention containing reduced coenzyme Q with these components.

When the fatigue reducing agent of the present invention containing reduced coenzyme Q is manufactured, the content of reduced coenzyme Q, the form of the product, and the storage method and mode, are determined appropriately depending on the design and the use of the commercial product of the fatigue reducing agent.

BEST MODE FOR CARRYING OUT THE INVENTION

The following Examples and Formulation Examples further illustrate the details of the present invention, but the scope of the present invention is not limited to these Examples and Formulation Examples.

Reference Example 1

A reducing reaction was carried out by adding 100 g of oxidized coenzyme $Q_{10}$ (purity 99.4%) and 60 g of L-ascorbic acid to 1000 g of ethanol and stirring at 78° C. Thirty hours later, the reaction mixture was cooled to 50° C., and 330 g of ethanol and 70 g of water were added while keeping the temperature at 50° C. This ethanol solution (containing 100 g of reduced coenzyme $Q_{10}$) was cooled to 2° C. at the rate of 10° C./h while stirring to obtain white slurry. The slurry thus obtained was filtered under reduced pressure, and the wet crystals were washed successively with cold ethanol, cold water, cold ethanol (cold media for washing were kept at 2° C.) and then dried under reduced pressure (20 to 40° C., 1 to 30 mmHg) to obtain 97 g of dry white crystals. All the operations except the drying under reduced pressure were carried out under a nitrogen atmosphere.

Reference Example 2

One hundred grams of oxidized coenzyme $Q_{10}$ was dissolved in 1000 g of heptane solution at 25° C. One hundred grams of sodium hyposulfite (purity of 75% or more) dissolved in 1000 ml of water was added slowly as a reducing agent to the oxidized coenzyme Q solution to carry out the reducing reaction at 25° C. and at pH 4 to 6. Two hours later, the water phase was removed from the reaction solution, and the heptane phase was washed 6 times with 1000 g of degassed saturated sodium chloride solution. Up to this point, all the operations were carried out under a nitrogen atmosphere. This heptane phase was subjected to solvent exchange under reduced pressure to prepare 7% (w/w) ethanol solution of reduced coenzyme $Q_{10}$ at 50° C. (containing 100 g of reduced coenzyme $Q_{10}$). Fifty grams of water was added to the ethanol solution and cooled to 2° C. at the rate of 10° C./h while stirring to crystallize reduced coenzyme $Q_{10}$. All the operations were carried out under a nitrogen atmosphere. The slurry obtained was filtered under reduced pressure, and the wet crystals were washed successively with cold ethanol, cold water, cold ethanol (the cold media used for washing were kept at 2° C.) and then dried under reduced pressure (20 to 40° C., 1 to 30 mmHg) to obtain 97 g of dry white crystals.

Example 1

It has been thought that coenzyme Q increases the energy supply to the muscle through its effect on the ATP generating system, and as a result, the anti-fatigue effect is expressed. Therefore it should be possible to predict the anti-fatigue effect of coenzyme Q by investigating the influences of administration of reduced coenzyme $Q_{10}$ on intramuscular coenzyme Q.

Reduced coenzyme $Q_{10}$ obtained in the Reference Example 1 (containing about 1% of oxidized coenzyme $Q_{10}$) was dissolved in soybean oil solution (reduced coenzyme $Q_{10}$/soybean oil solution=20 mg/ml) and orally administered to male SD rats (6 weeks of age) at a dose of 100 mg/kg of reduced coenzyme $Q_{10}$ (containing about 1% of oxidized coenzyme $Q_{10}$), once a day for 5 days. Five days later, the muscles of the femoral region were collected, and coenzyme Q level in the muscle was measured. The measurement of the coenzyme Q level in the muscle was performed using HPLC. The harvested rat muscle (0.2 g) was homogenized after the addition of coenzyme $Q_7$ (0.003 mg), ethanol (1 ml), distilled water (1 ml) and ferric chloride (0.01%), and then hexane (3 ml) was added. Coenzyme $Q_{10}$ was extracted from the homogenate after shaking. After repeating this extraction operation twice, the extract was brought to dryness by evaporating hexane out, re-dissolved in 0.25 ml ethanol and injected to HPLC. HPLC condition is as follows; column: YMC-Pack (ODS-A303), detection wavelength: 275 nm, mobile phase: methanol (88%), hexane (12%), flow rate: 1 ml/min. The measurement of the ratio of reduced coenzyme $Q_{10}$ and oxidized coenzyme $Q_{10}$ in the muscle was carried out as follows. The harvested rat muscle (0.2 g) was homogenized after the addition of distilled water (0.2 ml) and ethanol (0.8 ml), and the homogenate was extracted by adding hexane (1.2 ml). After evaporating hexane under a stream of nitrogen, the extract was re-dissolved in ethanol (0.2 ml) and injected to HPLC. The condition of the HPLC operation was the same as the above except that the electrochemical detector was used. Soybean oil was administered to the control group.

Comparative Example 1

Similarly oxidized coenzyme $Q_{10}$ was administered and then the coenzyme Q level in the muscle was measured.

TABLE 1

Level of Coenzyme Q in Muscle

| | Level of Coenzyme Q(µg/g) | | |
|---|---|---|---|
| | $Q_{10}$ | $Q_9$ | Total CoQ |
| Control Group | 0.73 ± 0.18 (100) | 9.62 ± 2.33 (100) | 10.35 ± 2.52 (100) |
| Reduced Coenzyme $Q_{10}$ Group | 1.57 ± 0.21 (215**) | 15.82 ± 2.89 (164*) | 17.39 ± 3.09 (168*) |
| Oxidized Coenzyme $Q_{10}$ Group | 1.34 ± 0.16 (184**) | 12.84 ± 2.03 (133) | 14.18 ± 2.18 (137) |

*$p < 0.05$,
**$p < 0.01$ Student t-test. Significantly different from the control group.

The result of the measurement of coenzyme Q in the muscle after administration of reduced or oxidized coenzyme $Q_{10}$ is shown in Table 1.

Example 2

The level of reduced coenzyme Q in the muscle was measured after administration of reduced coenzyme $Q_{10}$ in a manner similar to (Example 1).

Comparative Example 2

The level of reduced coenzyme Q in the muscle was measured after administration of oxidized coenzyme $Q_{10}$ in a manner similar to (Comparative Example 1).

TABLE 2

Level of Reduced Coenzyme Q in Muscle

| | Level of Reduced Coenzyme Q (µg/g) | | |
|---|---|---|---|
| | $Q_{10}$ | $Q_9$ | Total CoQ |
| Control Group | 0.32 ± 0.06 (100) | 3.28 ± 0.59 (100) | 3.60 ± 0.63 (100) |
| Reduced Coenzyme $Q_{10}$ Group | 0.39 ± 0.24 (122) | 5.32 ± 1.07 (162*) | 5.71 ± 1.16 (159*) |
| Oxidized Coenzyme $Q_{10}$ Group | 0.11 ± 0.10 (34**) | 2.34 ± 0.42 (71*) | 2.45 ± 0.44 (68*) |

*p < 0.05,
**p < 0.01 Student t-test. Significantly different from the control group.

The result of the measurement of the reduced coenzyme Q level in the muscle after administration of reduced or oxidized coenzyme $Q_{10}$ is shown in Table 2.

Example 3

Effect of reduced coenzyme $Q_{10}$ in young rats in the tread mill tests.

The anti-fatigue effect of reduced coenzyme $Q_{10}$ (note that it contained about 1% of oxidized coenzyme $Q_{10}$) was evaluated in male SD rats (7 weeks of age, n=10) using a tread mill. A rat was forced to run at a speed of 10 m/min on the tread mill machine (Type NK-73-4, Natsume Seisakusho Co., Ltd.). Then the speed was increased stepwise by 5 m/min in every 3 min, and the time when the rat could no longer run was measured (the maximum running time). The soybean oil solution of reduced coenzyme $Q_{10}$ according to the Reference Example 1 (reduced coenzyme $Q_{10}$/soybean oil solution=20 mg/ml) was prepared as a test substance and orally administered to rats as reduced coenzyme $Q_{10}$ (note that it contained about 1% of oxidized coenzyme $Q_{10}$) with a dose of 300 mg/kg. The maximum running times were measured before administration and 2 hours after administration and a prolongation of the maximum running time was calculated. Soybean oil was administered to the control group.

TABLE 3

Fatigue Reducing Effect in Young Rats

| | Maximum Running Time (Sec) | | |
|---|---|---|---|
| | Before administration | After administration | Time prolonged |
| Solvent Control | 1542 ± 105 (100) | 1598 ± 104 (100) | 56.1 ± 50.2 (100) |
| Reduced Coenzyme $Q_{10}$ 300 mg/kg | 1523 ± 97 (99) | 1719 ± 160 (108*) | 196 ± 127 (349**) |
| Oxidized Coenzyme $Q_{10}$ 300 mg/kg | 1543 ± 99 (100) | 1733 ± 107 (108**) | 190 ± 76 (339**) |

Note that reduced coenzyme $Q_{10}$ contained about 1% of oxidized coenzyme $Q_{10}$.
*p < 0.05,
**p < 0.01 Student t-test. Significantly different from the solvent control group.

The maximum running times are shown in Table 3. The maximum running time of rats was significantly prolonged by administration of reduced coenzyme $Q_{10}$ showing clearly that reduced coenzyme $Q_{10}$ has an anti-fatigue effect in young rats.

Comparative Example 3

Effect of Oxidized Coenzyme $Q_{10}$ in Young Rats in Tread Mill Tests

The anti-fatigue effect of oxidized coenzyme $Q_{10}$ was evaluated in young rats in a manner similar to (Example 3). The result indicated that the anti-fatigue effect of oxidized coenzyme $Q_{10}$ in the young rats was about the same as that of reduced coenzyme $Q_{10}$.

Example 4

Effect on Aged Rats in the Tread Mill Test

The anti-fatigue effect of reduced coenzyme $Q_{10}$ (containing about 1% of oxidized coenzyme $Q_{10}$) was evaluated in male SD rats (61 to 63 weeks of age, n=7) in a manner similar to (Example 3). This experiment was performed using a crossover method.

TABLE 4

Fatigue Reducing Effect on Aged Rats

| | Maximum Running Time (Sec) | | |
|---|---|---|---|
| | Before administration | After administration | Time prolonged |
| Solvent Control | 861 ± 123 (100) | 836 ± 121 (100) | −25 ± 24 |
| Reduced Coenzyme $Q_{10}$ 300 mg/kg | 861 ± 123 (100) | 958 ± 52* (115) | 97 ± 28** |
| Oxidized Coenzyme $Q_{10}$ 300 mg/kg | 861 ± 123 (100) | 875 ± 108 (105) | 14 ± 43 |

Note that reduced coenzyme $Q_{10}$ contained about 1% of oxidized coenzyme $Q_{10}$.
*p < 0.05,
**p < 0.01 Student t-test. Significantly different from the solvent control group.

The maximum running times are shown in Table 4. The maximum running time of rats is significantly prolonged one day after administration of reduced coenzyme $Q_{10}$ showing clearly that reduced coenzyme $Q_{10}$ also has an anti-fatigue effect on aged rats.

Comparative Example 4

The anti-fatigue effect of oxidized coenzyme $Q_{10}$ was evaluated in a manner similar to (Example 4). The results are shown in Table 4. Oxidized coenzyme $Q_{10}$ showed no prolongation effect on the maximum running time of aged rats, revealing that the anti-fatigue effect of oxidized coenzyme $Q_{10}$ is weak. The above results show that reduced coenzyme $Q_{10}$ demonstrates a wide range of anti-fatigue effect from young to aged animals, while oxidized coenzyme $Q_{10}$, which has been used in the past, demonstrates efficacy for young animals but has a poor efficacy for aged animals.

Formulation Example 1

Powder

Reduced coenzyme $Q_{10}$ (containing 1% of oxidized coenzyme $Q_{10}$) was dissolved in propanol and adsorbed to microcrystalline cellulose and then dried under reduced pressure. Powder formulation was prepared by mixing with corn starch under a stream of nitrogen.

| | |
|---|---|
| Reduced Coenzyme $Q_{10}$ | 9.9 parts by weight |
| Oxidized Coenzyme $Q_{10}$ | 0.1 parts by weight |
| Microcrystalline cellulose | 40 parts by weight |
| Corn Starch | 55 parts by weight |

Formulation Example 2

Capsule

After the powder formulation was prepared in a manner similar to Formulation Example 1, filling into a gelatin capsule was performed by a conventional method. The filled capsule was sealed, packed under a nitrogen atmosphere and stored under refrigeration.

| | |
|---|---|
| Reduced Coenzyme $Q_{10}$ | 19.8 parts by weight |
| Oxidized Coenzyme $Q_{10}$ | 0.2 parts by weight |
| Microcrystalline cellulose | 40 parts by weight |
| Corn Starch | 20 parts by weight |
| Lactose | 65 parts by weight |
| Magnesium Stearate | 3 parts by weight |
| Polyvinyl Pyrrolidon | 2 parts by weight |

Formulation Example 3

Soft Capsule

Reduced coenzyme $Q_{10}$ (containing 1% of oxidized coenzyme $Q_{10}$) melted at 50° C. was dissolved into corn oil heated to 50° C. Filling into soft capsules was performed by a conventional method.

| | |
|---|---|
| Reduced Coenzyme $Q_{10}$ | 49.5 parts by weight |
| Oxidized Coenzyme $Q_{10}$ | 0.5 parts by weight |
| Corn oil | 350 parts by weight |

Formulation Example 4

Tablet

Reduced coenzyme $Q_{10}$ (containing about 1% of oxidized coenzyme $Q_{10}$) was dissolved in propanol and adsorbed to microcrystalline cellulose and then dried under reduced pressure. This was mixed with corn starch, lactose, carboxymethyl cellulose and magnesium stearate under a nitrogen atmosphere. Then, aqueous solution of polyvinyl pyrrolidon was added to the mixture as a binder, and granulation was performed by a conventional method. After adding talc as a lubricant and mixing, tablet compression was performed on the granules. The tablets were packed under a nitrogen atmosphere and stored under refrigeration.

| | |
|---|---|
| Reduced Coenzyme $Q_{10}$ | 19.8 parts by weight |
| Oxidized Coenzyme $Q_{10}$ | 0.2 parts by weight |
| Corn Starch | 25 parts by weight |
| Lactose | 15 parts by weight |
| Calcium carboxymethyl cellulose | 10 parts by weight |
| Microcrystalline cellulose | 40 parts by weight |
| Polyvinyl Pyrrolidon | 5 parts by weight |
| Magnesium Stearate | 3 parts by weight |
| Talc | 10 parts by weight |

Formulation Example 5

Hydrophilic ointment containing reduced coenzyme $Q_{10}$ (containing 1% of oxidized coenzyme $Q_{10}$) with the following composition was prepared by a known method.

| | |
|---|---|
| Hydrophilic Ointment | 95.000% by weight |
| Reduced Coenzyme $Q_{10}$ | 0.990% by weight |
| Oxidized Coenzyme $Q_{10}$ | 0.010% by weight |
| Indomethacin | 1.000% by weight |
| Ascorbyl Stearate | 3.000% by weight |

Formulation Example 6

W/O type cream containing reduced coenzyme $Q_{10}$ (containing about 1% of oxidized coenzyme $Q_{10}$) with the following composition was prepared by a known method.

| | |
|---|---|
| Glycerol sorbitan fatty acid ester | 6.000% by weight |
| Microcrystalline Wax | 1.000% by weight |
| Olive Oil | 3.000% by weight |
| Liquid Parafin | 18.000% by weight |
| Magnesium Stearate | 1.000% by weight |
| Propyleneglycol | 3.700% by weight |
| Magnesium Sulfate ($MgSO_4.7H_2O$) | 0.700% by weight |
| Reduced Coenzyme $Q_{10}$ | 0.990% by weight |
| Oxidized Coenzyme $Q_{10}$ | 0.010% by weight |
| Indomethacin | 1.000% by weight |
| Desalted water | Up to 100.000% by weight |

Formulation Example 7

W/O type emulsion containing reduced coenzyme $Q_{10}$ (containing about 1% of oxidized coenzyme $Q_{10}$) with the following composition was prepared by a known method.

| | |
|---|---|
| Polyoxyethylene Glycerol Sorbitan Fatty Acid Ester | 3.600% by weight |
| Polyoxyethylene Fatty Acid Ester | 1.400% by weight |
| Stearyl Alcohol | 2.000% by weight |
| Mineral Oil, GP9 | 20.000% by weight |
| Paraben Mixture | as required |
| Magnesium Sulfate ($MgSO_4.7H_2O$) | 0.700% by weight |
| Reduced Coenzyme $Q_{10}$ | 0.990% by weight |
| Oxidized Coenzyme $Q_{10}$ | 0.010% by weight |
| Calcium Chloride ($CaCl_2$) | 0.85% by weight |
| Vitamin E | 1.000% by weight |
| Indomethacin | 1.000% by weight |
| Desalted water | Up to 100.000% by weight |

Formulation Example 8

W/O type lotion containing reduced coenzyme $Q_{10}$ (containing about 1% of oxidized coenzyme $Q_{10}$) with the following composition was prepared by a known method.

| | |
|---|---|
| Glycerol Sorbitan Fatty Acid Ester | 1.300% by weight |
| Polyoxyethylene Fatty Acid Ester | 3.700% by weight |
| Neutral Oil | 6.000% by weight |
| Liquid Parafin, GP9 | 14.000% by weight |
| Propylene Glycol | 3.800% by weight |
| Magnesium Sulfate ($MgSO_4.7H_2O$) | 0.700% by weight |
| Lipoic Acid | 1.500% by weight |
| Reduced Coenzyme $Q_{10}$ | 0.990% by weight |

| | |
|---|---|
| Oxidized Coenzyme $Q_{10}$ | 0.010% by weight |
| Ascorbic Acid | 2.000% by weight |
| Desalted water | Up to 100.000% by weight |

INDUSTRIAL APPLICABILITY

Since the fatigue reducing agent in the present invention has a constitution as described above, it demonstrates a superior effect of preventing and reducing fatigue as well as fatigue of the muscle. The agent has a strong fatigue reducing effect, especially for middle-aged and older persons, and thus it has a superior effect of maintaining physical fitness and health for middle-aged and older persons.

The invention claimed is:

1. A method for reducing fatigue in animals in the state of fatigue, wherein the animals are middle aged or older persons and wherein the fatigue is physical exhaustion, which comprises administering, to said animals, a fatigue reducing agent in a therapeutically effective amount comprising, as an active ingredient reduced coenzyme Q represented by the following formula (1) (wherein n represents 10)

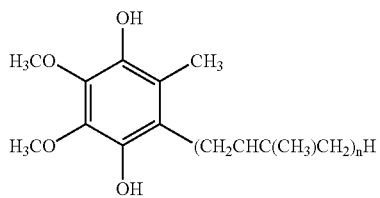

and oxidized coenzyme Q represented by the following formula (2) (wherein n represents 10)

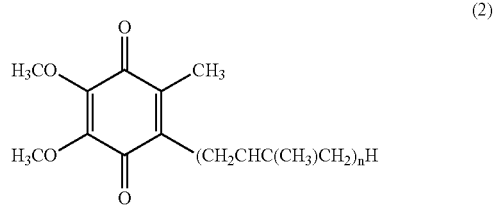

wherein a ratio of reduced coenzyme Q to total coenzyme Q is not less than 99% by weight, or reduced coenzyme Q represented by the above formula (1) (wherein n represents 10) in an amount of 100% based on total coenzyme Q.

2. The method according to claim 1, wherein the fatigue reducing agent is administered orally.

3. The method according to claim 1, wherein the active ingredient is reduced coenzyme Q and oxidized coenzyme Q and the ratio of reduced coenzyme Q to total coenzyme Q is 99% by weight.

4. The method according to claim 1, wherein the active ingredient is reduced coenzyme Q and oxidized coenzyme Q and the ratio of reduced coenzyme Q to total coenzyme Q is 99 to 99.5% by weight.

* * * * *